United States Patent [19]

Costa

[11] 4,321,414
[45] Mar. 23, 1982

[54] CATALYTIC HYDROGENATION OF GLYCOLALDEHYDE TO PRODUCE ETHYLENE GLYCOL

[75] Inventor: Lawrence C. Costa, Nanuet, N.Y.

[73] Assignee: The Halcon SD Group, Inc., New York, N.Y.

[21] Appl. No.: 181,493

[22] Filed: Aug. 26, 1980

[51] Int. Cl.³ ............................................. C07C 31/20
[52] U.S. Cl. ...................................................... 568/862
[58] Field of Search ........................................ 568/862

[56] References Cited

U.S. PATENT DOCUMENTS

3,935,284 1/1976 Kruse .................................. 568/862
4,024,193 5/1977 Kruse .................................. 568/862

OTHER PUBLICATIONS

R. A. Sanchez–Delgado et al., *J. Mol. Cat.*, vol. 6, pp. 303–305 (1979).
W. Strohmeier et al., *J. Organomet. Chem.*, vol. 145, pp. 189–194 (1978).
F. Joo et al., 25 *Inorg. Chemica Acta.*, L61–L62 (1977).

*Primary Examiner*—Natalie Trousof
*Assistant Examiner*—Frederick W. Pepper
*Attorney, Agent, or Firm*—William C. Long; David Dick; Riggs T. Stewart

[57] ABSTRACT

A process is provided for catalytic hydrogenation of glycolaldehyde to form ethylene glycol in liquid phase employing a homogeneous ruthenium catalyst and a basic promoter. Ethylene glycol is produced in excellent yields and selectivities, and the process permits use of mild temperature and pressure conditions.

11 Claims, No Drawings

CATALYTIC HYDROGENATION OF GLYCOLALDEHYDE TO PRODUCE ETHYLENE GLYCOL

CROSS-REFERENCE TO RELATED APPLICATIONS

This application is related to my co-pending application Ser. No. 163,550, filed June 27, 1980, the disclosure of which is hereby incorporated by reference.

BACKGROUND OF THE INVENTION

1. Field of the Invention

This invention relates to the production of ethylene glycol, and more specifically to the hydrogenation of glycolaldehyde in homogeneous catalysis systems.

2. Description of the Prior Art

Ethylene glycol is a chemical of acknowledged commercial importance, which is used widely in the preparation of anti-freeze compositions and in the manufacture of fiber, as well as in other uses. Ethylene glycol manufacturing processes of commercial interest have generally been based on ethylene oxide as a raw material. Other processes have been developed which make it possible to produce ethylene glycol, without the necessity for the intermediate manufacture of the epoxide, by a liquid phase reaction of olefin, carboxylic acid and molecular oxygen in the presence of a catalyst to produce carboxylic acid esters of the glycol. The glycol can then be liberated by hydrolysis of the esters.

Ethylene glycol has also been prepared by catalytic reaction of carbon monoxide and hydrogen. Thus, for example, U.S. Pat. No. 4,170,605 relates to a process for reacting carbon monoxide and hydrogen with certain ruthenium catalysts and a pyridine base ligand. However, high pressures are required for the reaction. Other processes include those disclosed in U.S. Pat. No. 4,170,606 (using an iridium complex catalyst) and published British Patent Application No. 2016006A (employing rhodium carbonyl phosphido cluster compounds).

Ethylene glycol has also been formed, albeit not commercially, by hydroformylation processes, wherein hydrogen and carbon monoxide are reacted with formaldehyde in the presence of certain catalyst systems. Exemplary of such processes are those disclosed in U.S. Pat. Nos. 4,079,085 (catalyst comprising cobalt carbonyl and rhodium) and 4,144,401 (catalyst comprising a rhodium compound), and 2,451,333 (catalyst compounds of Ni, Co, Mn, Fe, Cr, Cu, Pt, Mo, Pd, Zn, Cd, Ru, and especially Co). All of the hydroformylation processes, however, suffer from a relatively low yield of ethylene glycol and a poor selectivity to the desired product.

To avoid these disadvantages, European Patent Application No. 2,908 (1979) and German Pat. No. 2,741,589 (1978) sought to hydrogenate glycolaldehyde in the presence of certain hydrogenation catalysts to form ethylene glycol. The glycolaldehyde is formed by the hydroformylation of formaldehyde employing certain rhodium catalysts. European Patent Application No. 2,908 discloses hydrogenation of glycolaldehyde in aqueous solution employing Raney nickel, palladium or platinum heterogeneous catalysts. German Pat. No. 2,741,589 also envisions use of rhodium catalysts in hydrogenation of glycolaldehyde to form ethylene glycol, although the patent discloses that increased ethylene glycol yields can be obtained by use of palladium and nickel metal catalysts in the hydrogenation reaction.

In hydrogenations generally, it is well known that hydrogenation processes can be broadly classified into one of two categories, depending upon the physical phase in which the catalyst is present during the hydrogenation process. In the first type, the catalyst is essentially insoluble in the reaction medium; this is referred to as a heterogeneous hydrogenation process. In contrast, a homogeneous hydrogenation process describes a process in which the catalyst is essentially completely soluble in the reaction medium. Homogeneous hydrogenations typically allow use of milder process conditions than are necessary with heterogeneous catalysis, which would be industrially desirable.

Exemplary of the prior art homogenous hydrogenation processes employing ketones as feed are U.S. Pat. Nos. 3,935,284 (ruthenium triphenylphosphine complex plus a strong acid; hydrogenation of certain saccharides), and 4,024,193 (ruthenium triphenylphosphine complex and a strong acid; hydrogenation of described ketones, e.g., hydrogenation of 1,3-dihydroxy acetone to glycerol). Literature references to homogeneous hydrogenations of ketones to alcohols include R. R. Schrock, et al., Chem. Comm., pages 567–568 (1979); W. Strohmeier, et al., J. Organomet. Chem., Vol. 171, pages 121–129 (1970); P. Frediani, et al., J. Organomet. Chem., Vol. 150, pages 273–278 (1978); T. Tasumi, et al., 86 Chem. Abs., 170,448v (1977); and M. Gargano, et al., J. Organomet. Chem., Vol. 129, pages 239–242 (1977).

Ruthenium complexes containing sulfonated triphenylphosphine ligands have been reported to be catalysts in aqueous solutions for the homogeneous hydrogenation of oxo and olefinic groups in certain carboxylic acids. F. Joo, et al., 25 Inorg. Chemica. Acta. L61-L62 (1977) The complexes studied were HRu(O$_2$CCH$_3$)(Dpm)$_3$; and HRuCl(Dpm)$_3$, in which "Dpm" is a sulfonated triphenylphosphine group.

Various catalysts for the homogeneous hydrogenation of aldehydes have been proposed, such as various ruthenium compounds and complexes, in particular complexes of ruthenium containing triorganophosphine ligands and one or more of hydrido, halide, carbonyl, cyanate, thiocyanate and cyanide groups associated with the complex. Illustrative ruthenium complexes disclosed by the prior art for aldehyde hydrogenations are those disclosed in U.S. Pat. No. 3,454,644 (complexes of the formula L$_n$RuX$_2$ wherein L is a triphenylphosphine ligand, n is an integer of 3 to B 4 and X is a halogen or hydrogen); U.S. Pat. No. 3,857,900 (complexes of the formula L$_n$RuX$_y$ wherein L is again triphenylphosphine, n and y are each integers associated with the valence state of the ruthenium atom and X is halogen or "pseudohalogen", namely, cyanide, cyanate or thiocyanate); R. A. Sanchez-Delgado, et al., J. Mol. Cat., Vol. 6, pages 303–305 (1979) (RuHCl(CO)(P$\phi_3$)$_3$, RuHCl(P$\phi_3$)$_3$; RuCl$_2$(P$\phi_3$)$_3$, Ru(CO)$_3$(P$\phi_3$)$_2$); W. Strohmeier, et al., J. Organomet. Chem., Vol. 145, pages 189–194 (1978) (catalyst comprising RuCl$_2$(CO)$_2$(P$\phi_3$)$_2$.

Other ruthenium complexes have been developed and have been found useful catalysts in the hydrogenation of various alkenes and alkynes. See, e.g., P. L. Legzdins, et al., J. Chem. Soc. (A), 3322 (1970); D. Rose et al., J. Chem. Soc. (A) 2610 (1969); A. C. Skapski, et al., J. Chem. Soc. Dalton 390 (1974); and other references cited in my co-pending application Ser. No. 163,550.

SUMMARY OF THE INVENTION

According to the process of this invention, glycolaldehyde is hydrogenated to form ethylene glycol in high yields and in excellent selectivities by reacting glycolaldehyde in liquid medium with hydrogen in the presence of an effective amount of a catalyst comprising at least one member selected from the group consisting of (i) ruthenium complexes of the formula:

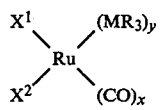

wherein x is an integer of 0 to 2, y is 2 or 3, M is P or As, R is aryl, $X^1$ is hydrogen, halide or pseudohalide and $X^2$ is halide or pseudohalide, with the proviso that $(x)^2+(y)^2$ is an integer of from 8 to 10, and (ii) ruthenium complexes of the formula:

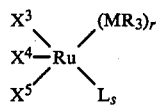

wherein M and R are as defined above, $X^3$, $X^4$ and $X^5$ are the same or different and are halide or pseudohalide, r is 2 or 3, s is 0 or 1, with the proviso that r must be 3 when s is 0, and L is an organic monodentate ligand, and in the additional presence of at least one promoter selected from the group consisting of basic compounds which are stronger bases than glycolaldehyde.

It has been surprisingly found that the promoters of this invention can effect high conversions of glycolaldehyde to ethylene glycol without the attendant formation of large amounts of acetal by-products which result when prior art ruthenium catalysts are employed in the absence of such basic promoters. These acetal by-products, which are formed by reaction of the glycolaldehyde with the product ethylene glycol, with hydroxylic solvents and with itself, are highly undesirable since they are not readily converted to ethylene glycol on recycle to the hydrogenation, but require further processing. The process of this invention is therefore a significant improvement in prior art hydrogenation processes.

DETAILED DESCRIPTION OF THE INVENTION

The ruthenium catalysts charged to the process of this invention comprise complexes of either formula (I):

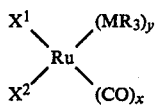

wherein x is an integer of 0 to 2, y is 2 or 3, M is P or As, $X^1$ is hydrogen, halide or pseudohalide, $X^2$ is halide or pseudohalide, and R is aryl, with the proviso that $(x)^2+(y)^2$ is an integer of from 8 to 10; or of the formula (II):

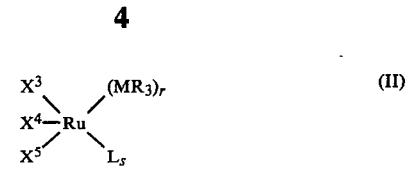

wherein M and R are as defined above, $X^3$, $X^4$ and $X^5$ are the same or different and are halide or pseudohalide, r is 2 or 3, s is 0 or 1, with the proviso that r must be 3 when s is 0, and L is an organic monodentate ligand.

The $X^1$ and $X^2$ groups in the formula (I) complexes can be the same or different, although only one of $X^1$ and $X^2$ can be hydrogen. Illustrative of suitable halide groups for the $X^1$, $X^2$, $X^3$, $X^4$ and $X^5$ substituents are Cl—, Br—, F— and I—, with Cl— being preferred. Pseudohalides are a recognized class of materials having halide-like properties in forming co-ordinate compounds and the like, including such members as $NCS^-$, $NCO^-$, $CN^-$, $NCSe^-$, $N_3^-$,

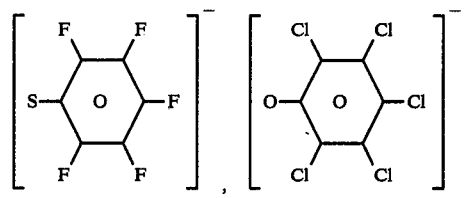

and the like.

The "R" groups comprise mono- or poly-nuclear aryl, such as phenyl, naphthyl and the like and can be substituted or unsubstituted. Suitable substituents include halo (Cl, Br, I, F), alkyl of 1 to 10 carbon atoms (e.g., methyl, ethyl, hexyl, decyl and the like), alkoxy of 1 to 8 carbon atoms (e.g., methoxy, ethoxy, propoxy and the like), acyl of 1 to 10 carbon atoms (e.g., acetyl, valeroyl, benzoyl and the like), cyano, tertiary amido of from 2 to 14 carbon atoms (e.g., N,N-dimethyl-carbamido, N,N-di-n-butyl-carbamido, N,N-diphenyl-carbamido and the like), carboxyalkyl of from 2 to 10 carbon atoms (e.g., carboxymethyl, carboxybutyl, carboxyheptyl and the like), hydroxy and cycloalkyl of from 3 to 8 carbon atoms (e.g., cyclopropyl, cyclohexyl, cyclooctyl and the like). Exemplary of such substituted R groups are tolyl, 2-ethyl phenyl, 3-methoxy phenyl, 2,4-dichloro phenyl, 3-carboxymethyl phenyl, 2,4-dihydroxy phenyl, para-cyclohexyl phenyl, 2-chloro-3-naphtyl, xylyl, and the like.

As indicated above, when x is 2, y must be 2, and when y is 3, x can be only 0 or 1. Hence, the sum of the squared values of these x and y values will, for the catalysts of formula (I) above, be 8, 9 or 10.

Suitable L ligands in the ruthenium catalysts of formula (II) above are organic compounds containing at least one nitrogen atom and/or at least one oxygen atom such that the atoms contain at least one pair of electrons which are available to form coordination bonds with the ruthenium. Examples of these organo L ligands are diamines, glycolic acid, alkoxy-substituted acetic acids, tetrahydrofuran, 1,2-dimethoxybenzene, alkyl ethers or alkylene glycols, alkanolamines, aminodiacetic acid, nitrilotriacetic acid, ethylenediaminetetraacetic acid, alkanols and ketones. Preferred L ligands are alkanols of 1 to 6 carbon atoms and ketones of 3 to 9 carbon atoms, such as methanol, ethanol, n-butyl alcohol, acetone, methyl ethyl ketone, methyl isobutyl ketone and the like.

Illustrative ruthenium halide catalysts charged to the hydrogenation in the process of this invention are:

| | |
|---|---|
| RuH(Cl) (P$\phi_3$)$_3$ | RuCl$_2$(P$\phi_3$)$_3$ |
| Br$_2$Ru(P$\phi_3$)$_3$ | ($\phi_3$P)$_2$Ru(CO)$_2$Cl$_2$ |
| ClRu[P—(O—C$_2$H$_5$)$_3$]$_3$ | RuCl$_3$[As—(p-tolyl)$_3$]$_2$ · CH$_3$OH |
| RuH(Cl) [P—(O—CN)$_3$]$_3$ | H(Br)Ru[P—(p-tolyl)$_3$]$_3$ |
| RuBr$_2$[P—(O—OH)$_3$]$_3$ | RuCl$_3$(As$\phi_3$)$_2$ · CH$_3$CCH$_3$ (O) |
| | I$_2$Ru(P$\phi_3$)$_3$ |
| H(Cl)Ru[P—(O—C$_2$H$_5$)$_3$]$_3$ | |
| HruCl(CO)(P$\phi_3$)$_3$ | | and the like.

Preferred catalysts of this invention are complexes of the formula (I) above wherein X$^2$ is chloro, X$^1$ is hydrogen or chloro, R is phenyl or alkyl-substituted phenyl of 7 to 16 carbon atoms, and M is P, and complexes of the formula (II) above wherein X$^3$, X$^4$ and X$^5$ are each chloro, M is P or As, R is phenyl or alkyl-substituted phenyl of 7 to 16 carbon atoms, and L is alkanol of 1 to 6 carbon atoms or ketone of 3 to 10 carbon atoms. Examples of preferred catalysts are HClRu(P$\phi_3$)$_3$, Cl$_2$Ru(P$\phi_3$)$_3$, Cl$_2$Ru[P-(para-tolyl)$_3$]$_3$, Cl$_3$Ru[P—(2,4-diethylphenyl)$_3$]$_2$ · CH$_3$CCH$_2$CH$_3$
$\quad\quad\quad\quad\quad\quad\quad\quad\quad\quad\quad\quad\quad\quad$ ||
$\quad\quad\quad\quad\quad\quad\quad\quad\quad\quad\quad\quad\quad\quad$ O and the like. Most preferred catalysts are complexes of the formula (I) above wherein X$^2$ is chloro, X$^1$ is hydrogen or chloro and MR$_3$ is triphenylphosphine.

The foregoing ruthenium catalysts can be prepared by known means, as for example by methods described in T. A. Stephenson, et al., *J. Inorg. Nuclear Chem.*, Vol. 28, 2285 (1966) and in U.S. Pat. No. 454,644.

Without intending to be limited by the following, it is believed that the ruthenium halide catalysts which are charged to the process of this invention undergo a series of reactions with hydrogen and glycolaldehyde during the hydrogenation reaction to form ruthenium halide intermediate complexes in which at least one atom of hydrogen and/or molecule of glycolaldehyde is bonded to the ruthenium catalysts at a site vacated by one or more ligands. However, the precise form(s) of such ruthenium halide intermediates is not known, and is not necessary for a full understanding or use of this invention.

The basic compounds which can be employed as promoters in the practice of this invention are stronger bases than glycolaldehye. Thus, the basic promoters are characterized by a base association constant ("K$_b$") which is greater than the base association constant of glycolaldehyde (as determined at 25° C.), i.e., the promoters possess a pK$_b$ which is less than the pK$_b$ of glycolaldehyde. As used herein, the term "K$_b$" is defined in reference to the equilibrium reaction:

as $$K_b = \frac{[B \cdot H^+]}{[B][H^+]}$$

wherein B is the base, B.H$^+$ is the conjugate acid of the base, [B.H$^+$] [B] and [H$^+$] are the concentrations in moles/liters, of B.H$^+$, B and H$^+$, respectively. The term "pK$_b$" is defined by the expression: pK$_b$= −log K$_b$.

Suitable basic promoters therefore include organic compounds such as heterocyclic tertiary amines of from 3 to 20 carbon atoms, polynuclear aromatic amines containing only tertiary nitrogen atoms, tertiary amines of the formula R$^1$(R$^2$)NR$^3$, sulfoxides of the formula R$^1$S(O)R$^2$, sulfones of the formula R$^1$(O)S(O)R$^2$, carbamates of the formula R$^1$OC(O)NR$^2$(R$^3$), ureas of the formula R$^1$(R$^4$)NC(O)NR$^2$(R$^3$) and amides of the formula ZC(O)NR$^2$(R$^3$), wherein Z is hydrogen or R$^1$, and wherein R$^1$, R$^2$, R$^3$ and R$^4$ in each of the above formulae can be the same or different and comprise alkyl of 1 to 20 carbon atoms, (e.g., methyl, ethyl, isopropyl, 2-ethylhexyl, decyl, dodecyl and the like), aryl of 6 to 14 carbon atoms (e.g., phenyl, naphthyl and the like), alkaryl or aralkyl of 7 to 20 carbon atoms (e.g., tolyl, xylyl, ethylphenyl, benzyl, ethylbenzyl, and the like) and cycloalkyl of 3 to 12 carbon atoms (e.g., cyclopropyl, cyclohexyl, cyclooctyl and the like), and the like. The R$^1$, R$^2$, R$^3$ and R$^4$ groups can be substituted by halo, alkoxy, tertiary amido, acyl, cyano, carboxylalkyl, hydroxy, alkyl and cycloalkyl groups which are discussed above as being suitable substituents for the "R" aryl groups of the ruthenium catalysts of the formulae (I) and (II).

Also suitable as promoters in the process of this invention are the hydroxides, oxides, carbonates, bicarbonates and carboxylates of metals of Group IA or IIA of the Periodic Table, (i.e., Li, Na, K, Rb, Cs, Be, Mg, Ca, Sr and Ba) quaternary ammonium, quaternary phosphonium and quaternary arsonium.

The carboxylate anion can be derived from a saturated aliphatic or aromatic carboxylic acid. Suitable aliphatic saturated carboxylic acids include those having from 1 to 20 carbon atoms, preferably from 1 to 10 carbon atoms, and more preferably from 1 to 4 carbon atoms. Aromatic carboxylic acids from which the above carboxylate anions can be derived include mono- and poly-nuclear aromatic acids having from 7 to 14 carbon atoms. The foregoing saturated aliphatic and aromatic carboxylic acids can be either straight-chained or branched-chained and can be substituted or unsubstituted. Suitable substituents include the halo, alkoxy, tertiary amido, acyl, cyano, carboxyalkyl, hydroxy, alkyl and cycloalkyl groups which are discussed above as being suitable substituents for the "R" aryl groups of the ruthenium catalysts of the formulae (I) and (II).

Exemplary of organic promoters are trimethyl amine, tri-n-propyl amine, ethyl-di-methyl amine, dimethyl-sec-butylamine, N-methyl-N-ethyl-aniline, N,N-dimethyl aniline, N,N-dimethyl acetamide, N,N-di-n-propyl formamide, N,N-dimethyl-N',N'-diethyl urea, 1-methyl pyrrolidin-2-one, 1-benzyl pyrrolidin-2-one, N,N-dimethyl propionamide, 1,5-dimethyl pyrrolidin-2-one, dimethyl sulfoxide, diethyl sulfoxide, dibenzyl sulfoxide, di-n-butyl sulfone, dimethylsulfone, N,N-diphenyl-methyl carbamate, N,N-dimethyl, N',N'- diphenyl urea, tri-n-octlamine, 1,8-diazabicyclo-2,2,2-octane, N,N-dimethyl benzamide, N,N-diphenyl formamide, tetramethylenesulfone, tetramethyl urea, 1,3-dimethyl-2-imidazolidinone, N-methyl-morpholine, 1,5-diazabicyclo[4.3.0]non-5-ene, 1,5-diazabicyclo[5.4.0]undec-5-ene, pyridine, pyridazine, pyrimidine, pyrazine, triazines, tetrazines, oxazines, indolenine, indiazene, 1,3-benzisodiazole, quinoline, isoquinoline, cinnoline, naphthyridine, phthalazine, benzontriazines, phenazine, isopyrrole, 2-isoimidazole, 1,2,3-isotriazole, and the like.

Exemplary of suitable inorganic and organic promoter salts are: MgO; BaO; $Na_2O$; $K_2O$; $Ba(OH)_2$; $Mg(OH)_2$; NaOH; LiOH; $Sr(OH)_2$; $CaCO_3$; $BaCO_3$; $Rb_2CO_3$; $Na_2CO_3$; $Cs_2CO_3$; $NaHCO_3$; $Mg(HCO_3)_2$; $KHCO_3$; alkali and alkaline earth metal carboxylates such as the acetates, butyrates, propionates, formates, hexanoates, benzoates, and toluates of Na, Mg, K, Ca, Cs Sr and Ba, sodium 2-ethyoxyiso-butyrate, potassium 2-methyl-pentanoate, magnesium naphthenate and the like; tetraethyl ammonium acetate; tetra-n-butyl phosphonium butyrate; tetramethyl arsonium carbonate; tetrapropyl ammonium bicarbonate; and the like.

Preferred base promoters are trialkyl amines of from 3 to 12 carbon atoms, triarylamines of from 18 to 30 carbon atoms, N,N-dialkyl amides having a total of from 3 to 13 carbon atoms, N,N-diarylamides having a total of from 14 to 31 carbon atoms, and metal carboxylates. Preferred metal carboxylates for use in this invention are members selected from the group consisting of Group IA and IIA metal salts of alkanoic monocarboxylic acids having from 1 to 4 carbon atoms. Still more preferred are metal carboxylates selected from the group consisting of sodium, magnesium, potassium and calcium salts of alkanoate monocarboxylic acids having from 1 to 4 carbon atoms. The acetate of the foregoing metals are especially preferred.

In addition to the glycolaldehyde, selected ruthenium catalyst and basic promoter, the liquid reaction medium will also contain a solvent for the glycolaldehyde and ruthenium catalyst. The solvents which are suitable for use will vary widely depending on the precise catalyst system selected and will include organic solvents such as alcohols, such as the lower alkanols (e.g., methanol, ethanol, isopropyl alcohol, propanol and the like) glycols (e.g., ethylene glycol, diethyle glycol, propylene glycol); aromatic solvents (such as benzene, toluene, the xylenes and the like); aromatic and aliphatic nitriles (such as acetonitrile, propionitrile, benzonitrile, and the like); amides (such as N,N-dimethyl formamide, N,N-dimethyl acetamide, N-methyl pyrollidinone, and the like); ketones (acetone, cyclohexanone, acetophenone, methyl isobutyl ketone, methyl ethyl ketone); esters (ethyl acetate, methyl laurate, methyl benzoate); ethers (diethyl ether, THF, diglyme, triglyme) and mixtures thereof. Preferred solvents are lower alkanols, lower alkylene glycols, ketones of 5 or fewer carbon atoms, esters of 6 or fewer carbon atoms, and ethers of at least 4 carbon atoms. Exemplary of preferred solvents are methanol, ethanol, isopropyl alcohol, propanol, butanol, pentanol, hexanol, ethylene glycol, propylene glycol, acetone, methyl ethyl ketone, ethyl acetate, diglyme and triglyme. From the foregoing, it will be apparent that the base promoter, if a liquid under the reaction conditions, can serve as the solvent for the reaction period. The selected organic solvent can also contain water, preferably in amounts of less than 50 wt. percent of the organic solvent.

The amount of solvent which is employed can vary widely, again depending on such factors as the precise solvent and ruthenium catalyst selected, in addition to temperature and other factors. Sufficient solvent should be employed to dissolve the selected ruthenium catalyst to provide the homogeneous catalyst system of this invention.

One great advantage of the improved process of this invention is the obtention of high yields and selectivities to ethylene glycol without the need for use of severe conditions of temperature or pressure. Thus, the mild temperature and pressure conditions which are possible avoid disadvantages associated with prior art processes. Generally, the temperature of the liquid reaction medium in this invention will range from about 50° to about 200° C., and more preferably from about 75° to 180° C., and most preferably from about 100° to 150° C. While temperatures of less than 50° C. can be employed, the rates of reaction are slower and tend to become uneconomic. Similarly, while temperatures greater than 200° C. can be employed, the rate of hydrogenation is not thereby substantially increased, and catalyst decomposition and by-product formation problems can occur to sometimes render such conditions uneconomic under some conditions.

Generally a hydrogen pressure of from about 15 to 2500 psig, and more preferably from about 100 to 2000 psig, and most preferably from 600 to 1500 psig, will be employed in the practice of this invention. It will also be understood that continuous or intermittent introduction of hydrogen to the reaction zone may be necessary to maintain the selected hydrogen pressure since hydrogen is consumed during the reaction.

The ruthenium catalysts of this invention are employed in catalytic quantities. Amounts of the catalyst from about 0.01 wt. % to about 20 wt. % based on the glycolaldehyde charged to the hydrogenation are satisfactory, although amounts from about 0.1 wt. % to about 5.0 wt. % on the same basis are preferred. Use of less than about 0.01 wt. % catalyst concentrations will be generally uneconomic due to the decreased rates of hydrogenation which can result. Also, while greater than 20 wt. % catalyst concentrations can be used, the added cost of the catalyst can outweigh the economic benefit to be derived from any increase in the rate of hydrogenation thereby obtained.

The methods by which the reactants and catalysts are contacted are not critical and can vary widely. Thus, one or more of the glycolaldehyde, selected solvents and catalysts can be premixed or charged directly to the reaction zone. Similarly, the gaseous hydrogen reactant can be premixed with one or more of the liquid components of the feed or can be separately charged to the reaction zone. The methods of contacting the gaseous hydrogen with the liquid reaction medium is not critical and illustrative are the conventional methods of gas sparging employing conventional gas sparging apparatus.

The concentration of glycolaldehyde in the liquid reaction medium is not critical and will vary widely depending upon such factors as temperature, solubility of glycolaldehyde in the selected solvent and other factors. Generally, the glycolaldehyde concentration will be from about 1.0 to about 20 wt. % of the total liquid reaction medium.

The basic promoter need not be soluble in the reaction medium, although at least partial solubility is preferred. The quantity of the selected basic promoter which should be employed in the liquid reaction medium will also vary widely. The base promoter will be generally used in an amount of at least about 0.01 wt. % and preferably at least about 0.1 wt. % of the total liquid reaction medium. The upper concentration of the basic promoter will be limited only by economic considerations. For example, where the basic promoter also comprises the solvent for the liquid reaction medium, the weight percent concentration of the basic promoter may be as much as 80 wt. % or more of the liquid reaction medium. The metal salts of Group IA and Group IIA metals, such as the hydroxide, oxides, carbonates, bicarbonates and carboxylates which have been mentioned above, will be generally used in an amount of from about 0.01 to 10 wt. % and preferably from about 0.1 to 5.0 wt. percent, of the total liquid reaction medium so as to provide the basic promoter in an amount of from about 1 to 2000 mole %, more preferably from about 100 to 1000 mole %, of the dissolved ruthenium catalyst, calculated as ruthenium.

The selected ruthenium catalyst will be generally employed in an amount sufficient to provide at least about 0.001 mole of ruthenium catalyst (calculated as ruthenium) per mole of glycolaldehyde present in the liquid reaction medium. While lower amounts can also be used, rates of hydrogenation are decreased. To overcome slower rates of hydrogenation to ethylene glycol which have been found to occur in hydrogenations at temperatures of less than 100° C. when the hydrogen pressure is less than 500 psig, the molar ratio of the selected ruthenium catalyst to glycolaldehyde present in the liquid reaction medium should preferably be at least 0.01:1 under these conditions.

The basic promoters of this invention can be preformed and introduced into the hydrogenation reaction zone. Alternatively, as when the basic promoter comprises one or more of the selected metal salts of Group IA or IIA, the metal salt can, if desired, be formed in situ in the hydrogenation reaction zone. Thus, for example, the metal carboxylates can be formed in the hydrogenation reaction zone by reaction of the corresponding carboxylic acid with a compound of the metal which is soluble in the reaction medium and in which the anion is a Lewis base whose conjugate acid is weaker than the carboxylic acid. Suitable metal compounds from which the metal carboxylates can be prepared include the alkoxides, carbonates, hydroxides, bicarbonates and the like of any of the foregoing metals. In the event a metal carboxylate salt is to be formed in situ in the liquid hydrogenation reaction medium, the selected carboxylic acid and metal compound, which are intended to react in the medium to form the carboxylate salt, should be introduced to the reaction medium in an amount sufficient to provide the desired quantity of carboxylate salt. Typically, the carboxylic acid and metal compound will be used in a molar ratio of from 1:1 to 5:1.

The period of time required for the hydrogenation reaction to reach completion will vary widely depending on such factors as reactant concentrations, $H_2$ pressure, temperature and the like, but will generally range from about 1 to 10 hours, more usually from about 2 to 4 hours. The liquid reaction medium can be agitated if desired during the course of the reaction to maintain intimate contacting of the gaseous hydrogen with the components of the liquid reaction mixture. Means by which such agitation can be performed are conventional and need not be described.

Subsequent to the reaction, the product mixture is separated and the desired product is recovered by conventional means such as fractional distillation, selective extraction, chromatographic techniques and the like. Unreacted glycolaldehyde can be recovered and recycled to the reaction, if desired. Similarly, the recovered ruthenium catalyst can also be recycled to the reaction since the activity of the catalyst is not thereby diminished.

The glycolaldehyde and selected ruthenium catalysts of this invention are preferably contacted in the substantial absence of molecular oxygen, since it has been found that while the ruthenium catalysts are relatively stable to oxygen when the catalysts are in solid form, they exhibit a sensitivity to molecular oxygen when the catalysts are dissolved in a liquid. By "substantial absence of molecular oxygen" herein is meant that the concentration of $O_2$ in the gas phase above the liquid reaction medium is maintained at a level of not greater than about 1.0 wt. % of oxygen. More preferably, the oxygen concentration in the gas phase is less than about 0.10 wt. %. The reaction can therefore be conducted in the presence of an inert gas for the reaction. Suitable inert gases are nitrogen, helium, argon and the like.

The process of this invention can be further illustrated by reference to the following Examples, wherein parts are by weight unless otherwise indicated. In each Example, the reaction vessel is flushed with $H_2$ to remove substantially all $O_2$ from above the liquid reaction mixture. All liquid samples are analyzed by gas chromatography. Yields, selectivities and conversions are reported based on the amount of glycolaldehyde charged to the reaction vessel. In Examples 2, 4, 6 and 8–13 the product mixture is found to contain no detectable acetal by-products, to a level of sensitivity of 0.01 wt. %.

EXAMPLE 1

Preparation of $RuCl_2(P\phi_3)_3$

To a 100 cc glass flask is added 50 mls. of methanol, 5.0 grams of triphenylphosphine and 1.0 gram of ruthenium trichloride hydrate. The resulting mixture is stirred and heated by means of an oil bath under an atmosphere of nitrogen to a temperature of 75° C. and maintained at that temperature for 6 hours. Tris(triphenylphosphine) ruthenium dichloride is formed as a brown insoluble powder, which is recovered by filtration (3.9 gram).

EXAMPLE 2

To a 200 ml. Parr pressure bomb equipped with a glass liner is charged 20 mls. of methanol, 0.30 gram (5.0 mmol) of glycolaldehyde, 0.02 gram of anhydrous sodium acetate, and 0.02 gram of $RuCl_2(P\phi_3)_3$, which is prepared as in Example 1. The contents of the bomb is stirred under gaseous nitrogen to dissolve the glycolaldehyde and the ruthenium halide catalyst and sodium acetate in the methanol solvent, and 800 psig of gaseous hydrogen is then charged to the reaction vessel. The vessel is then heated in an oil bath for 4 hours at 100° C., with continuous stirring of the liquid reaction mixture by means of a Teflon coating magnetic stirrer.

At the end of the above reaction time, a sample of the product mixture is taken and is analyzed by gas chromatography. Ethylene glycol is found to be produced in a yield of about 96% and a selectivity of about 96%, at a glycolaldehyde conversion of over 99%. No acetal by-product is detected.

EXAMPLE 3 FOR COMPARISON

The procedure of Example 2 is repeated except that the sodium acetate is omitted. At the end of the 4 hours of hydrogenation at 100° C., glycolaldehyde conversion is determined to be over 99%, but ethylene glycol is produced in a selectivity of only about 25%, and a yield of only about 25%. Selectivity to the dimethyl acetal of glycolaldehyde is found to be about 66%.

EXAMPLE 4

Preparation of RuCl$_2$(P-(p-tolyl)$_3$)$_3$

Using the procedure of Example 1, 50 mls. of methanol, 6.0 grams of tri-paratolylphosphine and 1.0 gram of ruthenium trichloride hydrate are stirred and heated at reflux under nitrogen for 24 hours to form tris(tri-paratolylphosphine) ruthenium dichloride as an insoluble powder which is recovered by filtration (4.2 grams).

Hydrogenation of Glycolaldehyde

The procedure of Example 2 is repeated employing 0.02 gram of tris(tri-paratolylphosphine) ruthenium dichloride as catalyst. After 4 hours of reaction at 100° C. and 800 psig, glycolaldehyde conversion is found to be 99% and ethylene glycol is found to be formed in a selectivity of about 93%. No acetal by-product is detected.

EXAMPLE 5 FOR COMPARISON

Example 4 is repeated employing 0.02 gram of tris(tri-paratolylphosphine) ruthenium dichloride in the hydrogenation of glycolaldehyde, except that the sodium acetate employed in Example 4 is omitted from the charge to the reactor. After 4 hours of hydrogenation at 800 psig and 100° C., glycolaldehyde conversion is found to be over 99%, ethylene glycol is found to be formed in a selectivity of about 70% and dimethyl acetal of glycolaldehyde is found to be formed in a selectivity of about 23%.

EXAMPLE 6

Preparation of RuCl$_2$[P-(p-methoxyphenyl)$_3$]$_3$

Following the procedure of Example 1, 50 mls. of methanol, 7.4 grams of tri-methoxyphenyl phosphine and 1.0 gram of ruthenium trichloride hydrate are admixed with stirring and heating at reflux temperature under an atmosphere of nitrogen for 4.0 hours. The solids which are formed as precipitate are recovered by filtration and are determined to comprise the desired tris(tri-para-methoxyphenylphosphine) ruthenium dichloride.

Hydrogenation of Glycolaldehyde

The procedure of Example 2 is repeated except that 0.02 gram of tris(tri-para-methoxyphenylphosphine) ruthenium dichloride, which is prepared as above, is employed as the catalyst, and the anhydrous sodium acetate is used in an amount of 0.01 gram. After 4 hours of hydrogenation at 100° C. and 800 psig hydrogen, the glycolaldehyde conversion is found to be 28% and ethylene glycol selectivity is found to be 51%. No acetal by-product of glycolaldehyde is detected.

EXAMPLE 7 FOR COMPARISON

The procedure of Example 6 is repeated for hydrogenation of glycolaldehyde except that no sodium acetate is charged to the hydrogenation reactor. After 4 hours at 100° C. and 800 psig, the hydrogenation is found to result in over 99% conversion of the glycolaldehyde, and ethylene glycol is found to produce only in a selectivity of about 5%. The selectivity to the dimethyl acetal of glycolaldehyde is found to be about 95%.

EXAMPLES 8–13

The procedure of Example 2 is repeated in separate experiments employing the indicated amount of the selected promoter. After 4 hours of hydrogenation at a temperature of 125° C. and a hydrogen pressure of 800 psig, the promoted tris(triphenyl phosphine) ruthenium dichloride catalyst is found to catalyze the hydrogenation of the glycolaldehyde in the amounts and to the products given in Table I below.

TABLE I

| Example No. | Promoter | Amount of Promoter (gms.) | Glycol-Aldehyde % Conv. | Selectivity to Ethylene Glycol (%) |
|---|---|---|---|---|
| 8 | Cs$_2$CO$_3$ | 0.07 | 99+ | 28 |
| 9 | (1) | 0.05 | 99+ | 87 |
| 10 | (2) | 0.02 | 99+ | 99 |
| 11 | (3) | 0.06 | 99+ | 95 |
| 12 | MgO | 0.02 | 99+ | 77 |
| 13 | Ba(OH)$_2$ | 0.03 | 99+ | 23 |

(1) 1,8-bis(dimethylamino) naphthalene
(2) 4-dimethylamino-pyridine
(3) mono potassium salt of phthalic acid No dimethyl acetal of glycolaldehyde is detected in any of the foregoing experiments.

EXAMPLE 14

Preparation of ($\phi_3$As)$_2$RuCl$_3$.CH$_3$OH

Following the procedure of Example 1, 1.0 gram of RuCl$_3$.H$_2$O, 6.1 gm. of triphenyl arsine and 50 ml. of methanol are charged to a 100 cc round bottom flask. The resulting mixture is heated with stirring at reflux under N$_2$ for 5 hours. The desired bis(triphenyl arsine) ruthenium trichloride .CH$_3$OH is formed as a green powder, which is recovered by filtration (3.7 gm).

Hydrogenation of Glycolaldehyde

Using the procedure of Example 2, 0.30 gm. of glycolaldehyde is admixed with 20 ml. of methanol, 0.05 gm. of ($\phi_3$As)$_2$RuCl$_3$.CH$_3$OH as catalyst and 0.50 gm. of sodium acetate. After hydrogenation at 150° C. with 800 psig H$_2$ for 4 hours, glycolaldehyde conversion is found to be over 99%, and ethylene glycol selectivity is 76%. Dimethylacetal of glycolaldehyde is formed in a selectivity of 3%.

EXAMPLE 15 FOR COMPARISON

When the hydrogenation of Example 14 is repeated, except that sodium acetate is omitted from the hydrogenation charge, the ethylene glycol selectivity is only 23% and the dimethyl acetal selectivity is 68%, at a glycolaldehyde conversion of over 99%.

EXAMPLE 16

The procedure of Example 2 is repeated using 0.5 gram glycolaldehyde, 0.10 gram of (P$\phi_3$)$_3$RuCl$_2$ as catalyst, 0.02 gram anhydrous sodium acetate and 20 ml. ethylene glycol as solvent. After hydrogenation at 125° C. for four hours employing 800 psig hydrogen, the glycolaldehyde conversion is found to be over 99% and selectivity to ethylene glycol is found to be 94%, with selectivity to 2-hydroxymethyl-1,3-dioxolane being found to be about 6%. The only products detected in the effluent are the foregoing acetal and ethylene glycol.

EXAMPLE 17 FOR COMPARISON

The procedure of Example 16 is repeated except that sodium acetate is omitted from the hydrgenation charge. After the four hours of hydrogenation at the indicated temperature and pressure, glycolaldehyde conversion is found to be over 99% and selectivity to the acetal by-product (2-hydroxymethyl-1,3 dioxolane) is found to be over 99%.

From the foregoing Examples it can be seen that the promoted ruthenium catalysts of this invention achieve very low quantities of acetal by-products. Preferably, the process of this invention forms a product mixture, following hydrogenation, which is substantially free of acetal by-product, that is, the acetal by-product is present in the effluent in an amount of less than 0.1 wt. % of the effluent. As used herein the term "acetal by-product" is intended to refer to acetals formed during the hydrogenation from whatever source, and therefore includes acetals formed by reaction of glycolaldehyde with an alcohol solvent used in the hydrogenation, or by reaction of glycolaldehyde with the ethylene glycol product, or by reaction of two or more molecules of glycolaldehyde.

The source of the glycolaldehyde which is employed as feed in the practice of this invention is not in any way critical. It has been found that effluents from prior art hydroformylation processes, in which glycolaldehyde is formed from formaldehyde, can be used to provide the glycolaldehyde feed to the hydrogenation process of this invention. In particular, the effluents formed in European Patent Application No. 2,908 and German Pat. No. 2,741,589, which have been referred to above and which are hereby incorporated by reference, containing glycolaldehyde together with the hydroformylation catalyst of these processes and any unreacted formaldehyde, can be charged directly to the process of this invention wherein the said glycolaldehyde feed is contacted under the above-disclosed hydrogenation conditions with the ruthenium halide catalyst system of this invention for formation of ethylene glycol in excellent yields and selectivities. It has been surprisingly found that the prior art hydroformylation catalysts, present in such glycolaldehyde feed to the process of this invention, do not adversely affect the performance of the instantly disclosed ruthenium catalysts for the hydrogenation of glycolaldehyde to ethylene glycol. Thus, the present invention offers the advantage of forming ethylene glycol from such hydroformylation effluents without the need to recover glycolaldehyde therefrom prior to hydrogenation and also without the need to remove any other constituents of the hydroformylation effluents prior to hydrogenation according to this invention.

In such prior art hydroformylation processes, formaldehyde, carbon monoxide and hydrogen are reacted at elevated temperature and pressure in the presence of the selected hydroformylation catalyst to form glycolaldehyde. The hydroformylation step is generally performed at temperatures of from about 50° to 250° C., at $H_2$ pressures of from about 500 to 5000 psig and at CO pressures of from about 500 to 5000 psig. Typically, the gaseous carbon monoxide and hydrogen are employed in a $CO:H_2$ ratio of from about 1:10 to about 10:1 and preferably from about 1:5 to about 5:1. Formaldehyde is generally employed in an amount sufficient to provide a formaldehyde concentration of from about 1 to 25 wt. % in the reaction medium.

The hydroformylation catalyst employed in the hydroformylation step can comprise any of the rhodium catalysts disclosed in European Patent Application No. 2,908 and German Pat. No. 2,741,589. Thus, the hydroformylation catalyst can be elemental rhodium or a compound, complex or salt thereof, and mixtures thereof, which can be used as such or deposited or bound to a solid support, such as molecular sieve zeolites, aluminum oxide, silicon dioxide, anion exchange resin or a polymeric ligand. German Pat. No. 2,741,589 discloses the active form of the rhodium catalyst to be a complex combination or bond with carbon monoxide, e.g., rhodium carbonyl, which has additional ligands. These additional ligands include halides (e.g., chloride) and organic ligands, such as the "L" ligands defined above, including compounds containing at least one nitrogen atom and/or at least one oxygen atom such that the atoms contain a pair of electrons which are available to form coordination bonds with rhodium. Examples of organic ligands include various piperazines, dipyridyls, N-substituted diamines, aminopyridines, glycolic acid, alkoxy-substituted acetic acids, tetrahydrofuran, dioxane, 1,2-dimethoxybenzene, alkyl ethers or alkylene glycols, alkanolamines, aminodiacetic acid, nitrilotriacetic acid, ethylenediaminetetraacetic acid, and ligands containing phosphorous such as trialkyl, triaryl and tricycloalkyl phosphites and triarylphosphines, as well as the analogous antimony and arsenic compounds. The rhodium hydroformylation catalyst can therefore be represented by the following formula (III):

$$RhX(CO)(PL_3')_2 \qquad (III)$$

wherein X is Cl, Br, I or F, and $PL_3'$ is a phosphine ligand in which each L is an organo group, such as aromatic or alkyl groups, with aryl and alkyl aryl phosphine ligands being generally preferred.

The quantity of hydroformylation catalyst which is used, solvents (if any), the precise form of the catalyst (for example, whether the catalyst is supported or unsupported and is homogenous or heterogeneous in the hydroformylation) and the like conditions are as disclosed in the foregoing European Patent Application No. 2,908 and German Pat. No. 2,741,589.

As indicated above, the effluent from the hydroformylation, containing glycolaldehyde, hydroformylation catalyst, and unreacted formaldehyde can be then charged as the glycolaldehyde feed to the hydrogenation process of this invention. The carbon monoxide gas employed in the hydroformulation should be removed prior to charging the effluent to the hydrogenation since it has been found that carbon monoxide gas can act as a poison for the ruthenium halide catalysts of this invention. Thus, it is preferred that the hydrogenation be performed in the substantial absence of gaseous carbon monoxide, i.e., less than 0.1 psig CO.

EXAMPLE 18

To a 200 ml. Parr pressure bomb equipped with a glass liner is charged 75 mls. of N,N-dimethylacetamide, 0.15 gram of tris(tri-phenylphosphine) rhodium monochloride (marketed by Strem Chemical Company), and 5.0 gram of para-formaldehyde. The contents of the bomb are stirred under gaseous nitrogen to dissolve the rhodium catalyst and paraformaldehyde in the N,N-dimethylacetamide solvent, and the reaction vessel is then pressured with 900 psig carbon monoxide and 900 psig gaseous hydrogen to provide a total pressure of 1800 psig above the liguid mixture. The vessel is then heated in an oil bath for 4 hours at 125° C., with continuous stirring of the liquid reaction mixture by means of a Teflon coated magnetic stirrer.

At the end of the above reaction time, a sample of the product mixture is taken and is analyzed by gas chromatography. Glycolaldehyde is found to be produced in an amount of 5.4 grams, which represents a glycolaldehyde yield of 54% based on the charged para-formaldehyde. Ethylene glycol is produced in a yield of only 1%, based on the para-formaldehyde charged.

The gases are vented from the reactor following the hydroformylation step to remove the gaseous carbon monoxide. The hydroformylation effluent is then divided into 3 equal portions. In separate runs, each portion is transferrd to a second 200 ml. Parr pressure bomb equipped with a glass liner and 0.05 gram of the selected ruthenium catalyst and 25 mls. of N,N-dimethyl actamide are charged. The contents of the second bomb are stirred under $N_2$ to dissolve the ruthenium catalyst, and 1200 psig of gaseous hydrogen is then charged to the reaction vessel. Following the procedure of Example 2, the hydrogenation is conducted with stirring at a temperature of 150° C. for 4 hours. The data thereby obtained are set forth in Table II below.

TABLE II

| Run No. | Catalyst* | Glycolaldehyde % Conversion | Ethylene Glycol % Selectivity |
|---|---|---|---|
| 1 | $(\phi_3 P)_3 RuCl_2$ | 76 | 75 |
| 2 | $Cl_2Ru[P-(p-tolyl)_3]_3$ | 88 | 77 |
| 3 | $(\phi_3 P_2)Ru(CO)_2Cl_2$ | 93 | 79 |

*Catalyst source:
Run 1 prepared as in Example 1.
Run 2 prepared as in Example 4.
Run 3 Strem Chemical Co.

The ethylene glycol which is produced by the process of this invention can, as it has been indicated above, be recovered by known means from the effluent withdrawn from the hydrogenation reaction vessel. If desired, a carboxylic acid can be added to the hydrogenation effluent in order to convert the ethylene glycol to the corresponding carboxylic acid ester of ethylene glycol. Preferably, however, the ethylene glycol is recovered, again by known means, from the hydrogenation effluent and then, in a separate step is reacted with a carboxylic acid, to form the corresponding carboxylic acid ester of ethylene glycol. Suitable carboxylic acids include saturated aliphatic monocarboxylic acids having from 1 to 20 carbon atoms, such as acetic acid, propionic acid, isobutyric acid, n-butyric acid, and the like.

The present invention, therefore, includes a two-step process for preparing carboxylic acid esters of ethylene glycol wherein, in a first step, glycolaldehyde is hydrogenated as above-described in the presence of a ruthenium halide ctalyst system of this invention, the product ethylene glycol is recovered and, in a second step, the ethylene glycol is reacted with a carboxylic acid in liquid medium to form the corresponding carboxylic acid ester of ethylene glycol. The conditions of temperature and pressure under which the second-step esterforming reaction is conducted are not critical and can vary widely. Generally, a temperature of from about 25° to 250° C. will be employed. An atmospheric, subatmospheric or superatmospheric pressure can be employed. The amount of carboxylic acid which is employed can also vary widely, although for a most complete reaction the carboxylic acid is preferably employed in an excess of that stoichiometrically required to react with the amount of ethylene glycol charged.

The presence of substantial amounts of strong acids, such as any of the strong mineral acids (e.g., hydrohalic acids, sulfuric, nitric, phosphoric and sulfonic acids) or any of the strong organic acids (e.g., trifluoroacetic acid) should be avoided in the process of this invention since it has been found that such acids cause the accelerated formation of unwanted by-products, e.g., unwanted acetal by-products. Accordingly, the liquid reaction medium of this invention is preferably substantially free of acids having an acid dissociation constant, $K_a$, of greater than $1 \times 10^{-2.5}$ at 25° C., i.e., acids having a $pK_a$ of less than 2.5. Preferably, the concentration of such acids should be less than 1 ppm.

It will be obvious that various changes and modifications can be made without departing from the invention, and it is intended, therefore, that all matter contained in the foregoing description shall be interpreted as illustrative only and not as limitative of the invention.

I claim:

1. A process for the hydrogenation of glycolaldehyde to form ethylene glycol which comprises contacting glycolaldehyde with hydrogen (a) in the presence of a liquid reaction medium in which there is dissolved at least one catalyst comprising a member selected from the group consisting of (i) ruthenium complexes of the formula:

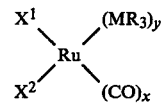

wherein x is an integer of 0 to 2, y is 2 or 3, M is P or As, R is aryl, $X^1$ is hydrogen, halide or pseudohalide, and $X^2$ is halide or pseudohalide, with the proviso $(x)^2 + (y)^2$ is an integer of from 8 to 10, and (ii) ruthenium complexes of the formula:

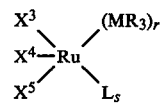

wherein M and R are as defined above, $X^3$, $X^4$ and $X^5$ are the same or different and are halide or pseudohalide, r is 2 or 3, s is 0 or 1, with the proviso that r must be 3 when s is 0, and L is an organic monodentate ligand, and (b) in the additional presence of at least one promoter selected from the group consisting of compounds which are stronger bases than glycolaldehyde as evidenced by a base association constant ("$K_b$") for said promoter at 25° C. which is greater than that for glycolaldehyde at 25° C.

2. The process according to claim 1 wherein said liquid medium is maintained at a temperature of from about 50° to 200° C.

3. The process according to claim 1 wherein said liquid medium additionally contains a solvent for glycolaldehyde selected from the group consisting of lower alkanols, aromatic solvents, glycols, aromatic and aliphatic nitriles, amides, ketones, esters and mixtures thereof.

4. The process according to claim 1 wherein the ruthenium catalyst is employed in an amount of at least about 0.001 mole of said catalyst, calculated as ruthenium, per mole of glycolaldehyde in said liquid medium.

5. The process according to claim 1 wherein $X^2$ is chloro, $X^1$ is hydrogen or chloro and M is P.

6. The process according to claim 1 wherein the promoter comprises at least one member selected from the group consisting of carboxylate salts of at least one metal of Group IA or IIA of the Periodic Table.

7. The process according to claim 6 wherein the carboxylate anion in said salt is derived from an aliphatic saturated carboxylic acid having from 1 to 20 carbon atoms or from an aromatic carboxylic acid having from 7 to 14 carbon atoms.

8. The process according to claim 6 wherein the metal carboxylate comprises a member selected from the group consisting of carboxylate salts of sodium, magnesium, potassium and calcium wherein the carboxylate moiety is derived from an alkanoate monocarboxylic acid having from 1 to 4 carbon atoms.

9. The process according to claim 6 wherein the metal carboxylate is employed in the liquid medium in an amount of from about 0.01 to about 10 wt. %, based on the total weight of the liquid reaction medium.

10. The process according to claim 1 wherein the promoter comprises at least one member selected from the group consisting of (i) ureas of the formula

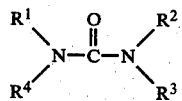

wherein $R^1$, $R^2$, $R^3$ and $R^4$ are the same or different and are alkyl of from 1 to 20 carbon atoms, aryl of 6 to 14 carbon atoms, alkaryl or aralkyl of 7 to 20 carbon atoms, and cycloalkyl of 3 to 12 carbon atoms, (ii) tertiary amines of the formula:

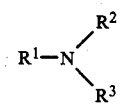

wherein $R^1$, $R^2$ and $R^3$ are as defined above; (iii) amides of the formula:

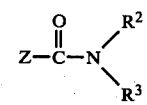

wherein Z is hydrogen or $R^1$, and wherein $R^1$, $R^2$ and $R^3$ are as defined above; (iv) sulfoxides of the formula:

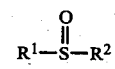

wherein $R^1$ and $R^2$ are as defined above; (v) sulfones of the formula:

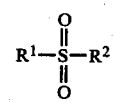

wherein $R^1$ and $R^2$ are as defined above; (vi) carbamates of the formula:

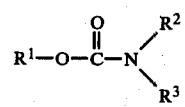

wherein $R^1$, $R^2$ and $R^3$ are as defined above; and (vii) heterocyclic tertiary amines of from 3 to 20 carbon atoms.

11. The process according to claim 1 wherein the glycolaldehyde is obtained by the hdroformylation of formaldehyde wherein formaldehyde is reacted with carbon monoxide and hydrogen in the presence of a hydroformylation catalyst.

* * * * *

UNITED STATES PATENT AND TRADEMARK OFFICE
CERTIFICATE OF CORRECTION

PATENT NO. : 4,321,414

DATED : March 23, 1982

INVENTOR(S) : Lawrence C. Costa

It is certified that error appears in the above-identified patent and that said Letters Patent are hereby corrected as shown below:

```
Col.  2, line 51 - delete "B"
Col.  5, last line of formula listing - "HruCl(CO)(PØ3)3"
                  should be --HRuCl(CO)(PØ3)3--
Col.  5, line 42 - "454,644" should be --3,454,644--
Col.  6, line  9 - "liters" should be --liter--
Col. 10, line 62 - "coating" should be --coated--
Col. 14, line 55 - "hydroformulation" should be
                  --hydroformylation--
Col. 15, line  6 - "liguid" should be --liquid--
Col. 15, line 21 - "transferrd" should be --transferred--
Col. 15, line 23-24 - "actamide" should be --acetamide--
Col. 18, line 42 - "hdroformylation" should be
                  --hydroformylation
```

Signed and Sealed this

Twenty-first Day of June 1983

[SEAL]

Attest:

DONALD J. QUIGG

Attesting Officer

Acting Commissioner of Patents and Trademarks